United States Patent
Hsu et al.

(10) Patent No.: US 8,377,116 B2
(45) Date of Patent: Feb. 19, 2013

(54) IMPLANTABLE MEDICAL DEVICE COATINGS WITH IMPROVED MECHANICAL STABILITY

(75) Inventors: Shaw Ling Hsu, Sunderland, MA (US); Yiwen Tang, San Jose, CA (US); Lothar W. Kleiner, Los Gatos, CA (US); Fuh-Wei Tang, Temecula, CA (US); Ni Ding, San Jose, CA (US); Syed Faiyaz Ahmed Hossainy, Fremont, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 795 days.

(21) Appl. No.: 12/052,452

(22) Filed: Mar. 20, 2008

(65) Prior Publication Data
US 2009/0240325 A1  Sep. 24, 2009

(51) Int. Cl.
*A61F 2/06* (2006.01)
(52) U.S. Cl. ..................................... 623/1.46; 623/1.44
(58) Field of Classification Search ............. 623/1, 1.11, 623/1.15, 1.44, 1.46
See application file for complete search history.

(56) References Cited

U.S. PATENT DOCUMENTS

| | | |
|---|---|---|
| 5,302,693 A | 4/1994 | Stricker et al. |
| 5,338,822 A | 8/1994 | Gruber et al. |
| 5,346,966 A | 9/1994 | Spinu et al. |
| 7,070,615 B1 | 7/2006 | Igaki |
| 2003/0125800 A1 | 7/2003 | Shulze et al. |
| 2006/0246108 A1 | 11/2006 | Pacetti et al. |
| 2007/0043434 A1 | 2/2007 | Meerkin et al. |
| 2008/0014240 A1* | 1/2008 | Gale et al. ..................... 424/422 |

FOREIGN PATENT DOCUMENTS

| | | |
|---|---|---|
| EP | 1 559 440 | 8/2005 |
| WO | WO 2007/116646 | 10/2007 |

OTHER PUBLICATIONS

Zhang et al. "Miscibility, crystallization and morphology of poly($\beta$-hydroxybutyrate)/poly (*d/l*—lactide) blends", Polymer, vol. 37, No. 2, pp. 235-241, 1996.
International Search Report for PCT/US2009/037375, mailed Apr. 13, 2010, 11 pgs.

* cited by examiner

*Primary Examiner* — Thomas J Sweet
*Assistant Examiner* — Seema Mathew
(74) *Attorney, Agent, or Firm* — Squire Sanders (US) LLP

(57) ABSTRACT

The present invention provides an implantable medical device coating that has improved stability, a medical device coated with such coating, and a method of increasing the stability of an implantable medical device coating, wherein the coating comprises a stereocomplex f poly(D-lactic acid) and poly(L-lactice acid).

13 Claims, No Drawings

IMPLANTABLE MEDICAL DEVICE COATINGS WITH IMPROVED MECHANICAL STABILITY

FIELD OF THE INVENTION

The present invention is directed to implantable medical device coatings that have improved mechanical stability and medical devices coated with such coatings.

BACKGROUND OF THE INVENTION

Polymers are generally characterized by their bulk properties such as tensile strength, yield stress, hardness, stiffness, elongation and gas permeability. Manufacturers use these properties to determine whether a particular polymer might be useful in a particular application. If, for example, a material that is hard and impact resistant is required, for use in say motorcycle helmets, a polymer that exhibits those bulk properties will be selected. If the intended use requires flexibility, toughness and elongation, as might be case with expandable coronary stents, a different type of polymer will be chosen.

Polymer characteristics are affected by the monomer types and composition, the polymer architecture and the molecular weight. The crystallinity of the polymer, an important factor in polymer biodegradation, varies with the stereoregularity of the polymer. For example, racemic D,L poly(lactide) or poly(glycolide) is less crystalline than the D or L homopolymers. Poly(lactide) (PLA) and its copolymers having less than 50% glycolic acid content are soluble in common solvents such as chlorinated hydrocarbons, tetrahydrofuran and ethyl acetate while poly(glycolide) (PGA) is insoluble in common solvents but is soluble in hexafluoroisopropanol.

The bulk properties of polymers can, however, change with time, a process known as aging. Aging can render a polymer unsuitable for its originally intended purpose and possibly cause a construct comprising that polymer to fail in use.

Polymers age by physical, chemical and/or electrical processes. Chemical aging results from exposure of a polymer to external factors such as air (oxygen), moisture, solvents, radiation, heat and light. Electrical aging results from voltage-induced stress that occurs at voltages usually in excess of about 3 kilovolts. Physical aging, which is the primary focus of this invention, results from residual and applied stresses.

This is true with polymer-coated implantable medical devices, e.g., drug-eluting stents (DESs), as well. The efficacy of DESs is related to their ability to release drugs in a controlled manner. One way this is accomplished is to include on the DES a rate-controlling layer, e.g., a topcoat layer, that is disposed over a drug reservoir layer and which comprises one or more polymers selected for their ability to mediate release of a particular drug or drugs from the underlying reservoir layer.

Another way to control drug release from a stent is by putting drugs in a drug reservoir layer that includes a polymeric matrix that mediates the release rate of the drug. Indeed, by manipulating the drug-to-polymer ratio, drug release can be controlled.

In both of these situations, however, the choice of polymer greatly affects the release of drugs from the device as well as the long term stability of the polymer on the device.

What is needed, therefore, is a method of mitigating the aging process of polymers so as to extend the useful life of coated medical devices as well as add an additional level of control over release rates of drug eluting devices. The present invention provides coatings that solve these and other problems in the art.

SUMMARY OF THE INVENTION

The present invention relates to an implantable medical device that includes a device body and a coating comprising a stereocomplex of poly(D-lactic acid) (PDLA) and poly(L-lactic acid) (PLLA) disposed over the device body, wherein the coating can form a primer layer, a reservoir layer, a topcoat layer or any combination thereof. The device body can be a stent.

In various aspects, the coating can form a primer layer disposed over the device body.

In various aspects, the coating can form a reservoir layer disposed over the device body. The reservoir layer can include one or more bioactive agents.

In various aspects, the coating can form a top-coat layer disposed over a reservoir layer. In this aspect, the reservoir layer can be formed from the coating.

Another aspect of the present invention relates to a method for increasing the stability of an implantable medical device coating that involves providing a device body and disposing a coating comprising a stereocomplex of poly(D-lactic acid) and poly(L-lactic acid) over the device body. The device body can be a stent.

In various aspects, the coating can form a primer layer disposed over the device body.

In various aspects, the coating can form a reservoir layer disposed over the device body.

In various aspects, the coating can form a top-coat layer disposed over a reservoir layer. In this aspect, the reservoir layer can be formed from the coating.

DETAILED DESCRIPTION

The present invention relates to an implantable medical device that includes a device body and a coating comprising a stereocomplex of poly(D-lactic acid) and poly(L-lactic acid) disposed over the device body, wherein the coating can form a primer layer, a reservoir layer, a topcoat layer or any combination thereof. The device body can be a stent.

As used herein, "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators, leads and electrodes for the preceding, implantable organ stimulators such as nerve, bladder, sphincter and diaphragm stimulators, cochlear implants, prostheses, vascular grafts, self-expandable stents, balloon-expandable stents, stent-grafts, grafts, PFO closure devices, arterial closure devices, artificial heart valves and cerebrospinal fluid shunts.

As used herein, "device body" refers to a fully formed implantable medical device with an outer surface to which no coating or layer of material different from that of which the device itself is manufactured has been applied. "Outer surface" means any surface, however spatially oriented, that is in contact with bodily tissue or fluids. An example of a "device body" is a BMS, i.e., a bare metal stent, which is a fully-formed usable stent that has not been coated with a layer of any material different from the metal of which it is made. It is to be understood that device body refers not only to BMSs but also to any uncoated device regardless of what it is made.

At present, preferred implantable medical devices for use with the coatings of this invention are stents.

A stent refers generally to any device used to hold tissue in place in a patient's body. Particularly useful stents are those used for the maintenance of the patency of a vessel in a patient's body when the vessel is narrowed or closed due to diseases or disorders including, without limitation, tumors (in, for example, bile ducts, the esophagus or the trachea/bronchi), benign pancreatic disease, coronary artery disease, carotid artery disease, renal artery disease and peripheral arterial disease such as atherosclerosis, restenosis and vulnerable plaque. For example, a stent can be used to strengthen the wall of the vessel in the vicinity of a vulnerable plaque (VP). VP refers to a fatty build-up in an artery thought to be caused by inflammation. The VP is covered by a thin fibrous cap that can rupture leading to blood clot formation. Thus, a stent can not only maintain vessel patency but can act as a shield against VP rupture. A stent can be used in, without limitation, neuro, carotid, coronary, pulmonary, aortic, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of bioactive agents to specific treatment sites in a patient's body. Indeed, bioactive agent delivery may be the sole purpose of the stent or the stent may be primarily intended for another use such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable. Due to the expansion of the stent, however, a stent coating must be flexible and capable of elongation.

Examples of stent materials include, without limitation, stainless steel, nitinol, tantalum, tantalum alloy, titanium, titanium alloy, cobalt chromium, alloy x, niobium, niobium alloy, zirconium and zirconium alloy.

Implantable medical devices of the invention, e.g., stents, will include a coating that comprises a stereocomplex of PDLA and PLLA disposed over the device body.

As used herein, "stereocomplex" refers to a polymer structure comprising individual PDLA and PLLA polymer chains connected supra-molecularly.

As used herein, "supra-molecular" interactions refer to noncovalent interactions between chemical groups on different polymer chains.

As used herein, "stereocomplex" can also refer to a stereoselective interaction between two complementing stereoregular polymers, that interlock and form a new composite, demonstrating altered physical properties in comparison to the parent polymers.

As used herein, a material that is described as a layer "disposed over" an indicated substrate, e.g., a device body, refers to a relatively thin coating of the material applied directly to essentially the entire exposed surface of the indicated substrate. The term "disposed over" may, however, also refer to the application of the thin layer of material to an intervening layer that has been applied to the substrate, wherein the material is applied in such a manner that, were the intervening layer not present, the material would cover substantially the entire exposed surface of the substrate.

As used herein, "primer layer" refers to a coating consisting of a polymer or blend of polymers that exhibit good adhesion characteristics with regard to the material of which the device body is manufactured and good adhesion characteristics with regard to whatever material is to be coated on the device body. A primer layer is applied directly to a device body to serve as an intermediary layer between the device body and materials to be affixed to the device body. Examples, without limitation, of primers include silanes, titanates, zirconates, silicates, parylene, vinyl alcohol copolymers, acrylic acid copolymers, methacrylic acid copolymers, polyethyleneamine, polyallylamine, acrylate and methacrylate polymers with poly(n-butyl methacrylate). In some presently preferred embodiments of the invention, the primer layer can include a stereocomplex of the invention.

As used herein, "reservoir layer" refers either to a layer of one or more bioactive agents applied to a medical device neat or to a layer of polymer or blend of polymers that has dispersed within its three-dimensional structure one or more bioactive agents. A polymeric reservoir layer is designed such that, without limitation, by elution or as the result of biodegradation of the polymer, the bioactive agent is released from the layer into the surrounding environment. The reservoir layer generally comprises a biocompatible polymer that can be biostable or biodegradable and can be hydrophobic or hydrophilic. Suitable polymers are known to those skilled in the art. In some presently preferred embodiments of the invention, the reservoir layer can include a stereocomplex of the invention.

As used herein, "biocompatible" refers to a polymer that both in its intact, as synthesized state and in its decomposed state, i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

The bioactive agent, also referred to herein as a drug or a therapeutic agent, can be selected from a group that includes, without limitation, an antiproliferative agent, an anti-inflammatory agent, an antineoplastic, an antimitotic, an antiplatelet, an anticoagulant, an antifibrin, an antithrombin, a cytostatic agent, an antibiotic, an anti-allergic agent, an anti-enzymatic agent, an angiogenic agent, a cyto-protective agent, a cardioprotective agent, a proliferative agent, an ABC A1 agonist or an antioxidant.

As used herein, "topcoat layer" refers to a polymeric layer that is applied over a drug reservoir layer to modify a bioactive agent's rate of release into the environment. A rate-controlling layer may be used simply to "tune" the rate of release to exactly that desired by the practitioner or it may be a necessary adjunct to the construct because the polymer or blend of polymers with which the bioactive agent is compatible, with regard to coating as a drug reservoir layer, may be too permeable to the bioactive substance resulting in too rapid release and delivery of the bioactive substance into a patient's body. The term "top-coat layer" also refers to an outermost layer that is in contact with the external environment and that is disposed as the final layer of a series of layers. In some presently preferred embodiments of the invention, the topcoat layer can include a stereocomplex of the invention.

It is to be understood that an implantable medical device of the invention will necessarily include a stereocomplex of PDLA and PLLA in at least one of the coating layers, although any combination is encompassed by the present invention. For example, the primer layer "pl", reservoir layer "rl" and topcoat layer "tl" can all be comprised of a stereocomplex of the invention, depicted by pl+rl+tl. Also possible would be a coating depicted by pl+tl, or pl+rl or rl+tl. The determination of which layer or layers will include a stereocomplex of the invention, however, will be left to the practitioner.

No matter which layer design is used by a practitioner, a stereocomplex of PDLA and PLLA coated onto a device will exhibit a higher Tg and Tm than either homopolymers or copolymers of PDLA and/or PLLA, and thus will exhibit increased stability with improved mechanical properties. A stent coated with such a stereocomplex, therefore, will be less prone to physical aging since the coating will be quasi-crystalline. In addition, from the perspective of controlled release of bioactive agents, a coating comprising a stereocomplex will have less variation in subsequent agent release rates.

Methods of forming a stereocomplex of PDLA and PLLA are known to those skilled in the art. Two exemplary methods, however, would initially involve either dissolving the polymers in a solvent or melting and mixing the polymers together. The resulting mixture would then be stored under conditions at which the polymers form a complex and either precipitate out of solution or solidify from the molten state.

Solvents which can be used to dissolve polymers for formation of stereocomplexes include, without limitation, dioxane, chloroform tetrahydrofuran, ethyl acetate, acetone, N-methylpyrrolidone, ethyl and methyl lactate, ethyl acetate and mixtures of these solvents, and other solvents, such as water, short chain alcohols and carboxylic acids (5 carbon atoms or less). The particle size of the precipitate is controlled by the selected solvent, the drug, polymer concentrations and the reaction conditions (temperature, mixing, volume etc.), all of which will be ascertainable without undue experimentation by those skilled in the art.

Bioactive agents of the invention can be incorporated onto or into the stereocomplexes. They can be coupled to the stereocomplexes by ionic, hydrogen or other types of bond formation, including covalent bond formation. The bioactive agent can be incorporated into the stereocomplexes when the polymers are mixed together in solution or melted, so that the molecules are entrapped within the polymer complex as it precipitates or cools. They can also be physically mixed with the stereocomplexes as they are coated onto a device. Alternatively, the bioactive agents can be coupled to the stereocomplexes after formation of the complexes.

Methods of disposing a stereocomplex coating of the invention over the device and/or over other coating layers include, without limitation, dip-coating, spray coating (including electrospray coating), powder coating, using an ink jet and other techniques known to those skilled in the art.

Another aspect of the present invention relates to a method for increasing the stability of an implantable medical device coating that involves providing a device body and disposing a coating comprising a stereocomplex of poly(D-lactic acid) and poly(L-lactic acid) over the device body. The device body can be a stent.

In various aspects, the coating can form a primer layer disposed over the device body.

In various aspects, the coating can form a reservoir layer disposed over the device body.

In various aspects, the coating can form a top-coat layer disposed over a reservoir layer. In this aspect, the reservoir layer can be formed from the coating.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true sprit and scope of this invention.

What is claimed is:

1. An implantable medical device comprising:
    a device body; and
    a coating disposed over the device body, wherein the coating comprises a reservoir layer and further comprises a primer layer or a topcoat,
        wherein the primer layer or the topcoat comprises a stereocomplex of poly(D-lactic acid) and poly(L-lactic acid).

2. The implantable medical device according to claim 1, wherein the device body comprises a stent.

3. The implantable medical device according to claim 1, wherein the coating comprises a primer layer disposed over the device body.

4. The implantable medical device according to claim 1, wherein the coating comprises a reservoir layer disposed over the device body.

5. The implantable medical device according to claim 4, wherein the reservoir layer comprises one or more bioactive agents.

6. The implantable medical device according to claim 1, wherein the coating comprises a top-coat layer disposed over a reservoir layer.

7. The implantable medical device according to claim 6, wherein the reservoir layer comprises a stereocomplex of poly(D-lactic acid) and poly(L-lactic acid).

8. A method for increasing the stability of an implantable medical device coating comprising:
    providing a device body; and
    disposing a coating over the device body;
    wherein the coating comprises a reservoir layer and further comprises a primer layer or a topcoat,
        wherein the primer layer or the topcoat comprises a stereocomplex of poly(D-lactic acid) and poly(L-lactic acid).

9. The method according to claim 8, wherein the device body comprises a stent.

10. The method according to claim 8, wherein the coating comprises a primer layer disposed over the device body.

11. The method according to claim 8, wherein the coating comprises a reservoir layer disposed over the device body.

12. The method according to claim 11, wherein the coating comprises a top-coat layer disposed over a reservoir layer.

13. The method according to claim 12, wherein the reservoir layer comprises a stereocomplex of poly(D-lactic acid) and poly(L-lactic acid).

* * * * *